US012623052B2

(12) United States Patent　　　　(10) Patent No.:　US 12,623,052 B2

Modley et al.　　　　　　　　　　　　(45) Date of Patent:　　May 12, 2026

(54) INDWELLING CATHETER SYSTEM

(71) Applicant: University of Galway, Galway (IE)

(72) Inventors: Richard Modley, Plymouth (GB); Tim Jones, Salthill (IE); Michelle Tierney, Sixmilebridge (IE)

(73) Assignee: University of Galway, Galway (IE)

( * ) Notice: Subject to any disclaimer, the term of this patent is extended or adjusted under 35 U.S.C. 154(b) by 318 days.

(21) Appl. No.: 18/511,584

(22) Filed: Nov. 16, 2023

(65) Prior Publication Data

US 2024/0082538 A1　　Mar. 14, 2024

Related U.S. Application Data

(63) Continuation of application No. 17/928,785, filed as application No. PCT/EP2021/064428 on May 28, 2021.

(30) Foreign Application Priority Data

May 30, 2020　　(EP) .................................... 20177632

(51) Int. Cl.
　　*A61M 25/02*　　　　(2006.01)
　　*A61M 25/00*　　　　(2006.01)
　　*A61M 39/26*　　　　(2006.01)

(52) U.S. Cl.
　　CPC .... *A61M 25/0017* (2013.01); *A61M 25/0067* (2013.01); *A61M 25/02* (2013.01); *A61M 39/26* (2013.01)

(58) Field of Classification Search
　　CPC ............ A61M 1/04; A61M 1/71; A61M 1/84; A61M 2025/0213; A61M 2025/0286;

(Continued)

(56) References Cited

U.S. PATENT DOCUMENTS 5,738,656 A　　4/1998　Wagner
8,347,881 B2 *　1/2013　Tanaka .............. A61M 16/0429
　　　　　　　　　　　　　　　　128/207.29

(Continued)

FOREIGN PATENT DOCUMENTS

| CN | 101124009 A | 2/2008 |
| CN | 105209087 A | 12/2015 |
| JP | 2008538185 A | 10/2008 |
| JP | 2012183352 A | 9/2012 |
| WO | 2006090148 A1 | 8/2006 |
| WO | 2011112291 A1 | 9/2011 |
| WO | 2014174218 A1 | 10/2014 |

OTHER PUBLICATIONS

International Search Report and Written Opinion issued in counterpart PCT Application No. PCT/EP2021/064428 dated Sep. 30, 2021 (fifteen (15) years).

*Primary Examiner* — Kai H Weng

(74) *Attorney, Agent, or Firm* — E. Eric Mills; Nicholas P. Stadnyk; Maynard Nexsen PC

(57)　　　　　　ABSTRACT

An indwelling pleural catheter system comprises an indwelling catheter device (2) comprising a catheter tube (7) with a fenestrated distal end (7A) configured to reside in the pleural cavity of a subject and a connection hub (10) fluidically coupled to a proximal end (7B) of the catheter tube, a skin anchoring member (3) to anchor the connection hub (10) to the skin of the subject, and optionally a detachable ambulatory suction module (4) configured for detachable attachment to the connection hub (10). The suction module (4) comprises a fluid inlet (19) configured for fluidic coupling to the catheter tube (7) through the connection hub (10) and a fluid outlet (20) configured for detachable fluidic coupling to a pleural fluid drainage system (5) to drain pleural fluid through the detachable ambulatory suction module. The detachable ambulatory suction module is configured to exert a negative pressure in the catheter tube upon detachment of the pleural fluid drainage system from the suction module. Treatment of pleural effusion using the system of the inven- (Continued)

tion is described. An indwelling catheter system for draining fluid from the peritoneal cavity, and methods of treating ascites, is also described.

25 Claims, 10 Drawing Sheets

(58) Field of Classification Search
CPC .. A61M 2039/0252; A61M 2039/0261; A61M 2039/0288; A61M 2210/101; A61M 25/0017; A61M 25/0067; A61M 25/007; A61M 25/02; A61M 27/00; A61M 39/0247; A61M 39/26
See application file for complete search history.

(56) References Cited

U.S. PATENT DOCUMENTS

| | | | |
|---|---|---|---|
| 2005/0234390 A1* | 10/2005 | Buckman | A61B 17/3415 |
| | | | 604/22 |
| 2007/0078442 A1 | 4/2007 | Mayse | |
| 2011/0288534 A1* | 11/2011 | Aguirre | A61J 15/0026 |
| | | | 604/535 |
| 2014/0330228 A1 | 11/2014 | Kerr | |
| 2019/0143094 A1 | 5/2019 | DeMeritt | |
| 2019/0381220 A1 | 12/2019 | Locke et al. | |

* cited by examiner

INDWELLING CATHETER SYSTEM

CROSS REFERENCE TO RELATED APPLICATIONS

This application is a continuation application of Ser. No. 17/928,785 filed Nov. 30, 2022, which is a 35 U.S.C. § 371 U.S. national phase entry of International Patent Application No. PCT/EP2021/064428 having an international filing date of May 28, 2021, which claims the benefit of European Patent Application No. 20177632.5 filed May 30, 2020, each of which is incorporated herein by reference in its entirety.

FIELD OF THE INVENTION

The present invention relates to an indwelling catheter system. The invention also relates to a method of treating a pleural effusion in a subject that employs an indwelling pleural catheter system

BACKGROUND TO THE INVENTION

A pleural effusion is a condition characterised by a build-up of excess fluid in the pleural cavity, the cavity defined by the parietal and visceral membranes that surround the lungs and act to lubricate and facilitate breathing. Normally the pleural cavity contains a small amount of fluid. An excess of fluid can cause chest pain, cough, dyspnea and orthopnea. The condition can be caused by many factors, including heart failure, pulmonary embolism, cirrhosis, and open-heart surgery. Other causes include pneumonia, cancer, kidney disease, and inflammatory conditions.

Common treatments for pleural effusion include thoracentesis (removal of fluid using a syringe), tube thoracostomy (removal of fluid using a chest tube which remains in situ for several days), pleural drain (removal of fluid using a long-term indwelling catheter), and a pleurodesis procedure. The latter involves irritating the pleural membranes, either chemically or mechanically, and has a success rate of 70-90% resulting in the prevention of recurrence of pleural effusions. The treatment is highly invasive, requires lengthy hospitalisation, and is contraindicated for patients with a trapped lung.

The insertion of an indwelling pleural catheter (IPC) provides is a less invasive, ambulatory alternative compared to the pleurodesis procedure to manage effusions. However, IPC insertion does require an invasive tunnelling procedure, involving two incisions being made, to secure the catheter under the skin. Furthermore, current IPCs are designed to drain the pleural fluid only and, do not contain dedicated mechanisms to prevent fluid from reaccumulating. As a result, many people being treated with IPCs may have them in place for up to a year.

It is an object of the invention to overcome at least one of the above-referenced problems.

SUMMARY OF THE INVENTION

The Applicant has addressed the problems of the prior art by providing an indwelling pleural catheter system that can perform pleural fluid drainage and also promote pleurodesis by the extended application of negative pressure therapy to the pleural cavity after a drainage step. The application of negative pressure to the pleural cavity using an indwelling catheter functions to draw the parietal and visceral membranes together promoting pleurodesis. The catheter system comprises a fenestrated catheter tube configured for placement within the pleural cavity with a connection hub at a proximal end, and a detachable suction module configured to attach to the connection hub that is adjustable between three configurations. In a first configuration (drainage), the suction module provides fluidic connection between the connection hub and the pressurised drainage system, and pleural fluid is drained under pressure through the suction module. In a second configuration (negative pressure therapy), the drainage system is detached from the suction module, but the suction module remains negatively pressurised and exerts a negative pressure in the catheter tube, applying a negative pressure therapy to the pleural cavity. A third configuration (resting) comprises detachment of the suction module from the connection hub, maintaining the negative pressure in the catheter tube. In another aspect, the invention provides a catheter system for draining fluid from a cavity in a subject defined by parietal and visceral membranes (for example a pleural or peritoneal cavity).

In a first aspect, the invention provides an indwelling pleural catheter system comprising:

an indwelling catheter device comprising a catheter tube with a fenestrated distal end configured to reside in the pleural cavity of a subject and a connection hub fluidically coupled to a proximal end of the catheter tube;

a skin anchoring member to anchor the connection hub to the skin of the subject; and a detachable ambulatory suction module configured for detachable attachment to the connection hub and comprising:

a fluid inlet configured for fluidic coupling to the catheter tube through the connection hub;

a fluid outlet configured for detachable fluidic coupling to a pleural fluid drainage system to drain pleural fluid through the detachable ambulatory suction module; and typically an actuable closure configured to close the fluid outlet upon actuation, wherein the detachable ambulatory suction module is generally configured to exert a negative pressure in the catheter tube upon actuation of the closure.

Thus, the system of the invention is configured to allow drainage of liquid from the pleural cavity in a first configuration (e.g. drainage system attached to the catheter via the ambulatory suction module, with the closure open), apply a pre-defined negative pressure therapy to the pleural cavity by the suction module in a second configuration (e.g. drainage system detached from suction module, closure in suction module closed to pressurise the suction module and apply a negative pressure to the pleural cavity through the catheter). A third resting configuration involves detachment of the ambulatory suction module from the connection hub.

In any embodiment, the detachable ambulatory suction module comprises a negative pressure chamber, wherein the fluid inlet is fluidically coupled to the fluid outlet by the negative pressure chamber. Typically, the negative pressure chamber has a volume of at least 10, 15, 20, 25 or 30 cc. This provides a simple and effective arrangement for negatively pressurising the suction module and catheter tube to allow negative pressure therapy of the pleural cavity.

In any embodiment, the actuable closure is configured to close by detachment of the pleural fluid drainage system from the detachable ambulatory suction module and open upon attachment of the pleural fluid drainage system and the detachable ambulatory suction module. The drainage system may include a connector with a projecting conduit configured to project into the fluid outlet of the ambulatory suction module and open the closure. The closure may be, for example, a duck bill valve or any other type of valve such as a cross valve or disc valve, or a combination of a cross valve and disc valve.

In any embodiment, the detachable ambulatory suction module comprises a bleed valve configured to maintain a threshold negative pressure in the catheter tube, typically upon detachment of the pleural fluid drainage system from the detachable ambulatory suction module. The bleed valve may be configured to open when the pressure in the suction module exceeds the threshold negative pressure allowing air into the suction module until the threshold negative pressure is reached whereupon it closes.

In any embodiment, the bleed valve is configured to maintain a threshold negative pressure in the catheter tube of 20-300 mmHg, 20-200 mmHg or 20-140 mmHg.

In any embodiment, the system is configured to monitor pressure in the system, for example in the ambulatory suction module or catheter tube, and modify the negative pressure exerted by the fluid drainage system in response to the monitored pressure. Generally the ambulatory suction module or catheter tube comprises a pressure sensor. Generally, the system comprises a processor operatively coupled to the pressure sensor and the fluid drainage system (for example coupled to a pump of the fluid drainage system). Generally the processor is configured to compare the pressure sensed by the pressure sensor with a reference pressure, and actuate the fluid drainage system to modify the negative pressure exerted by the fluid drainage system based on the comparison. In one embodiment, the system is configured to prevent the negative pressure in the system (for example in the ambulatory suction module or catheter tube) dropping below negative 140 mmHg (ie negative 141 mm Hg, negative 142 mm Hg etc.). In one embodiment, the system is configured to maintain the negative pressure in the ambulatory suction module or catheter tube at a pressure of negative 20-300 mmHg, 20-200 mmHg, or 20-140 mmHg.

The connection hub is generally provided at a proximal end of the catheter tube and provides a hub for connection of the catheter tube with the ambulatory suction module. In any embodiment, the connection hub comprises one or more closures configured to open upon attachment of the detachable suction module with the connection hub and close upon detachment of the connection hub with the detachable suction module.

In any embodiment, the connection hub comprises at least two spaced apart closures, one of which may be a duckbill valve.

In any embodiment, the fluid inlet of suction module protrudes from the surface of the suction module and is configured to project into the connection hub to open the closure or closures.

In any embodiment, the skin anchoring member is separate from and configured for coupling with the connection hub. This allows the skin anchoring member be attached to the skin prior to attachment to the connection hub. The coupling may be a snap-fit coupling, a friction fit coupling, a threaded screw coupling, or any other type of coupling.

In another embodiment, the skin anchoring member may be integrally formed with the connection hub and optionally configured to rotate relative to the connection hub.

In any embodiment, the skin anchoring member comprises a through-lumen for receipt of the fenestrated catheter tube.

In any embodiment, the system comprises an external housing configured for attachment (typically detachable attachment) to the connection hub and comprising a connection hub embracing housing with a through lumen for receipt of the connection hub to expose a proximal end of the connection hub and a base configured to abut and preferably attach the skin of the subject around the connection hub. This provides a seal around the connection hub protecting the connecting hub, anchoring member and incision from coming into contact with fluids or dirt when the system is in use.

In any embodiment, the base of the cover comprises an adhesive element for attaching the base of the cover to the skin of the subject around the connection hub. The cover may include a peel-away backing.

In any embodiment, the external housing and detachable suction module may be dimensioned to facilitate coupling. For example, the detachable suction module may have a recessed base and the external housing may have be dimensioned to nest within the recessed base of the detachable suction module. The recessed base of the detachable suction module may be concave and the external housing may be convex.

In any embodiment, a portion of the fluid inlet of the detachable suction module projects proud of the recessed base of detachable suction module. This allows the fluid inlet project into the connection hub and establish fluidic communication with the catheter through the connection hub.

In any embodiment, the indwelling pleural catheter system is configured for assembly into a number of different configurations including:

a resting configuration in which the detachable suction module is not fluidically connected to the connection hub;

a drainage configuration in which the detachable suction module is fluidically connected to the connection hub and the pleural fluid drainage system allowing drainage of pleural fluid under pressure through the catheter device and detachable ambulatory suction module; and a negative pressure therapy configuration in which the detachable suction module is fluidically coupled to the connection hub, not fluidically coupled to the pleural fluid drainage system, and negatively pressurized.

In any embodiment, the detachable suction module and the external housing are configured for coupling together. The coupling may be a snap-fit coupling, a friction fit coupling, a threaded screw coupling, or any other type of coupling.

In any embodiment, the system comprises a pleural fluid drainage system configured for fluidic coupling to the outlet of the detachable suction module. The pleural fluid drainage system generally comprises a pleural fluid collection vessel and a pump configured to draw pleural fluid from the pleural cavity into the collection vessel. The drainage system in some embodiments does not have a pump, and may be configured to draw pleural fluid from the pleural cavity by other means, including gravity.

In any embodiment, the system comprises a needle, cannula and peel-away catheter/dilator.

In any embodiment, the connection hub and/or cover comprises a UV light configured to direct light on the catheter tube and/or the skin. Typically the cover comprises a UV light configured to direct light on the catheter tube and/or the skin.

In any embodiment, the connection hub and/or cover comprises an antibacterial coating.

In any embodiment, the connection hub and skin anchoring member are configured for coupling together. The coupling may be a snap-fit coupling, a friction fit coupling, a threaded screw coupling, or any other type of coupling.

In a second aspect, the invention provides an indwelling catheter system for draining fluid from a body cavity of a subject defined by a parietal membrane and a visceral membrane (for example a pleural or peritoneal cavity), comprising:

an indwelling catheter device comprising a catheter tube with a fenestrated distal end configured to reside in the cavity of the subject and a connection hub disposed on a proximal end of the catheter tube and configured to fluidically couple the catheter tube with a fluid drainage device; and a skin anchoring member having a through lumen for receipt of the catheter tube, an anchor element configured for anchoring to the skin of the subject, and a coupling element configured to couple the skin anchoring member to the connection hub.

In any embodiment, the system comprises an external housing configured for attachment (typically detachable attachment) to the connection hub and comprising a connection hub embracing housing with a through lumen for receipt of the connection hub to expose a proximal end of the connection hub and a base configured to abut and optionally attach to the skin of the subject around the connection hub.

In any embodiment, the base of the cover comprises an adhesive element for attaching the cover to the skin of the subject around the connection hub. The base may include a backing member for the adhesive element.

In another aspect the invention provides an ambulatory suction module suitable for use with an indwelling pleural or peritoneal catheter, comprising a housing having:

a fluid inlet configured for detachable fluidic coupling to a connection hub of an indwelling pleural catheter;

a fluid outlet configured for detachable fluidic coupling to a pleural fluid drainage system; and an actuable closure configured to close the fluid outlet upon actuation, wherein the detachable ambulatory suction module is typically configured to exert a negative pressure in the catheter tube upon actuation of the closure.

In any embodiment, the detachable ambulatory suction module comprises a negative pressure chamber, wherein the fluid inlet is fluidically coupled to the fluid outlet by the negative pressure chamber. Typically, the negative pressure chamber has a volume of at least 10, 15, 20, 25 or 30 cc.

In any embodiment, the actuable closure is configured to close by detachment of the pleural fluid drainage system from the detachable ambulatory suction module and open upon attachment of the pleural fluid drainage system and the detachable ambulatory suction module. The drainage system may include a connector with a projecting conduit configured to project into the fluid inlet of the suction module and open the closure. The closure may be, for example, a duck bill valve or any other type of valve such as a cross valve or disc valve or a combination thereof.

In any embodiment, the detachable ambulatory suction module comprises a bleed valve configured to maintain a threshold negative pressure in the catheter tube upon detachment of the pleural fluid drainage system from the detachable ambulatory suction module. The bleed valve opens when the pressure in the suction module exceeds the threshold negative pressure.

In any embodiment, the bleed valve is configured to maintain a threshold negative pressure in the catheter tube of 20-300 mmHg, 20-200 mmHg, or 20-140 mmHg.

In any embodiment, the system comprises a pressure sensor to determine negative pressure in the system. The sensor may be located in the ambulatory suction module or in the catheter tube (or any other part of the system such as a fluidic conduit coupling the drainage system with the ambulatory suction module).

In another aspect, the invention provides an indwelling pleural catheter system according to the invention for use in treating a pleural effusion, typically a recurrent pleural effusion, in a subject.

In another aspect, the invention provides an indwelling pleural catheter system according to the invention for use in treating a pleural effusion, typically a recurrent pleural effusion, in a subject by forming or promoting the formation of a pleurodesis.

In another aspect, the invention provides a method of treating a pleural effusion in a subject that employs an indwelling pleural catheter with a fenestrated distal end, the method comprising the steps of:

generating an incision in the chest of the subject at an incision point;

inserting the indwelling pleural catheter into the chest of the subject through the incision until the fenestrated distal end of the catheter tube is disposed in the pleural cavity and a proximal end of the catheter is disposed on a surface of the chest of the subject; and a pleural liquid drainage step comprising applying a first negative pressure to the pleural cavity through the pleural catheter to drain fluid from the pleural cavity, characterised in that the method comprises a negative pressure therapy step comprising applying a second negative pressure to the pleural cavity through the pleural catheter after the drainage step.

In any embodiment, the second negative pressure is less than or the same as the first negative pressure. In any embodiment, the second negative pressure applied to the catheter tube is 20-300 mmHg, 20-200 mmHg or 20-140 mmHg.

In any embodiment, the method comprises maintaining a negative pressure in the pleural cavity during transiting from the first negative pressure to the send negative pressure.

In any embodiment, the method comprises a step of anchoring the proximal end of the catheter to the skin at the incision.

In any embodiment, the method comprises a resting step during which neither the first or second negative pressure is applied to the pleural catheter.

In any embodiment, the method comprises a step of fluidically coupling a detachable suction module to a proximal end of the indwelling pleural catheter, wherein the detachable suction module is configured for detachable fluidic attachment to a pleural liquid drainage system configured to apply the first negative pressure to the pleural catheter, wherein the drainage step comprises fluidically attaching the detachable suction module to the pleural fluid drainage system.

In any embodiment, the detachable suction module is configured to apply the second negative pressure to the pleural catheter when it is fluidically detached from the pleural fluid drainage system, wherein the negative pressure therapy step comprises fluidically detaching the pleural fluid drainage system from the detachable suction module.

In any embodiment, the resting step comprises detaching the detachable suction module from the pleural catheter.

In another aspect, the invention provides a method of treating a pleural effusion in a subject that employs an indwelling pleural catheter system according to the invention, the method comprising the steps of:

generating an incision in the chest of the subject at an incision point;

inserting the catheter tube of the indwelling catheter device into the chest of the subject through the incision until the fenestrated distal end of the catheter tube is disposed in the pleural cavity and the connection hub is disposed on a surface of the chest at the incision point; anchoring the connection hub to the skin of the subject with the skin anchoring member;

draining pleural fluid from the pleural cavity under negative pressure by coupling the connection hub and the detachable ambulatory suction module to the pleural fluid drainage system and actuating the pleural fluid drainage system; and applying negative pressure therapy to the pleural cavity through the catheter tube by de-coupling the pleural fluid drainage system from the detachable ambulatory suction module and applying a negative pressure exerted by the detachable ambulatory suction module.

In any embodiment, the method includes a step of coupling an external housing to the connection hub prior to coupling the connection hub to the detachable ambulatory suction module.

In any embodiment, the method comprises a resting step comprising de-coupling the detachable ambulatory suction module from the connection hub to maintain a negative pressure in the catheter tube.

In any embodiment, the method comprises the catheter tube being inserted through a single cavity in the chest.

In any embodiment, the skin anchoring member is separate from and configured for coupling with the connection hub, and the method comprises the steps of anchoring the skin anchoring member to the skin of the subject at the incision point, inserting the catheter tube into the chest of the subject, and coupling the connection hub to the anchored skin anchoring member.

In any embodiment, the skin anchoring member comprises a central aperture for receipt of the catheter tube, and the method includes the step of anchoring the skin anchoring member to the skin such that the central aperture of the skin anchoring member overlies the incision point in the chest of the subject; whereby the step of inserting the catheter tube into the chest of the subject is performed through the central aperture of the skin anchoring member.

In any embodiment, the drainage step, negative pressure therapy step and resting step are performed at least once every 48 hours, 24 hours, 18 hours, or 12 hours.

In any embodiment, the negative pressure therapy step lasts 1-24, 1-12, 1-8, 1-5, 1-3, 1-2 or 0.5 to 1 hours.

In any embodiment, the steps of inserting the catheter tube into the pleural cavity and anchoring the connection hub comprise the steps of:

anchoring the skin anchoring member at the incision point;

inserting a needle and introducer through the incision and through the chest wall into the pleural cavity;

withdrawing the needle leaving the introducer in place;

advancing a guidewire through the introducer and into the pleural cavity;

removing the introducer over the guidewire and leaving the guidewire in place;

advancing a peel-away catheter/dilator into the pleural cavity over the guidewire;

removing the dilator part of the catheter/dilator and the guidewire;

advancing the catheter tube through the peel-away catheter until the connection hub abuts the peel-away catheter;

removing the peel-away catheter; and coupling the connection hub to the skin anchoring member.

In another aspect, the invention provides a method of treating a pleural effusion in a subject, comprising a step of applying negative pressure therapy to a pleural cavity of the subject by an indwelling pleural catheter for a period of time to promote pleurodesis.

Generally, the method comprises draining pleural fluid from the pleural cavity for a period of time prior to the negative pressure therapy step.

In one embodiment, the negative pressure therapy step comprises applying a negative pressure of 20-300 mmHg, 20-200 mmHg or 20-140 mmHg to the pleural cavity of the subject through the indwelling pleural catheter.

In one embodiment, the negative pressure therapy step is performed for 1-24, 1-12, 1-8, 1-5, 1-3, 1-2 or 0.5 to 1 hours.

In one embodiment, the method comprises a plurality of negative pressure treatments, optionally including a plurality of drainage treatment.

In another aspect, the invention provides a method of treating a condition associated with fluid build-up in a body cavity of a subject defined by a parietal membrane and a visceral membrane, for example ascites or pleural effusions, that employs a system of the invention, comprising the steps of:

generating an incision in the abdomen or chest of the subject at an incision point;

inserting the catheter tube of the indwelling catheter device into the abdomen or chest of the subject through the incision until the fenestrated distal end of the catheter tube is disposed in the body cavity and the connection hub is disposed on a surface of the skin at the incision point;

anchoring the connection hub to the skin of the subject with the skin anchoring member; and draining fluid from the cavity under negative pressure by coupling the connection hub with the fluid drainage system and actuating the fluid drainage system.

Other aspects and preferred embodiments of the invention are defined and described in the other claims set out below.

BRIEF DESCRIPTION OF THE FIGURES

FIG. 8 is a sectional view of the ambulatory suction module of FIG. 7.

FIG. 9 is a sectional view of the connection hub, catheter and external housing of FIG. 7.

FIGS. 10A to 10K show the use of the system of the invention to treat pleural effusion, in which:

FIG. 10A shows a patient with the indwelling pleural catheter device inserted with the distal catheter tube in the pleural cavity (not shown) and the connection hub anchored to the skin of the patient (not shown) and external housing coupled to the connection hub (not shown), and the ambulatory suction module and pleural fluid drainage system on the table and fluidically connected;

FIG. 10B shows a hygiene cap being removed from the external housing by the patient;

FIG. 10C shows the suction module being coupled to the connection hub by the patient;

FIG. 10D shows the patient actuating the drainage pump to drain fluid from the pleural cavity through the pleural catheter and ambulatory suction module;

FIG. 10E illustrates the drainage step with the patient in a sitting position while the drainage step is performed;

FIG. 10F illustrates the patient detaching the connector of the pleural fluid drainage system from the ambulatory suction module to terminate the drainage step and initiate the negative pressure therapy step;

FIG. 10G illustrates the negative pressure therapy step where the ambulatory suction module remains fluidically connected to the connection hub exerting negative pressure on the pleural cavity to promote pleurodesis. During this step, the patient may be ambulatory as illustrated;

FIG. 10H illustrates the patient detaching the ambulatory suction module from the connection hub to terminate the negative pressure therapy step and initiate the resting step. Upon detachment the valves in the connection hub close to fluidically seal the indwelling pleural catheter.

FIG. 10I shows the patient with the connection hub and external housing exposed and a hygiene cap on the table;

FIG. 10J shows the patient about to apply the hygiene cap to the external surface of the connection hub and external housing; and FIG. 10K shows the patient during the resting step with the hygiene cap covering the external surface of the connection hub and external housing. Although the patient is shown sitting, the patient may also be ambulatory during this step.

DETAILED DESCRIPTION OF THE INVENTION

Figure 1:
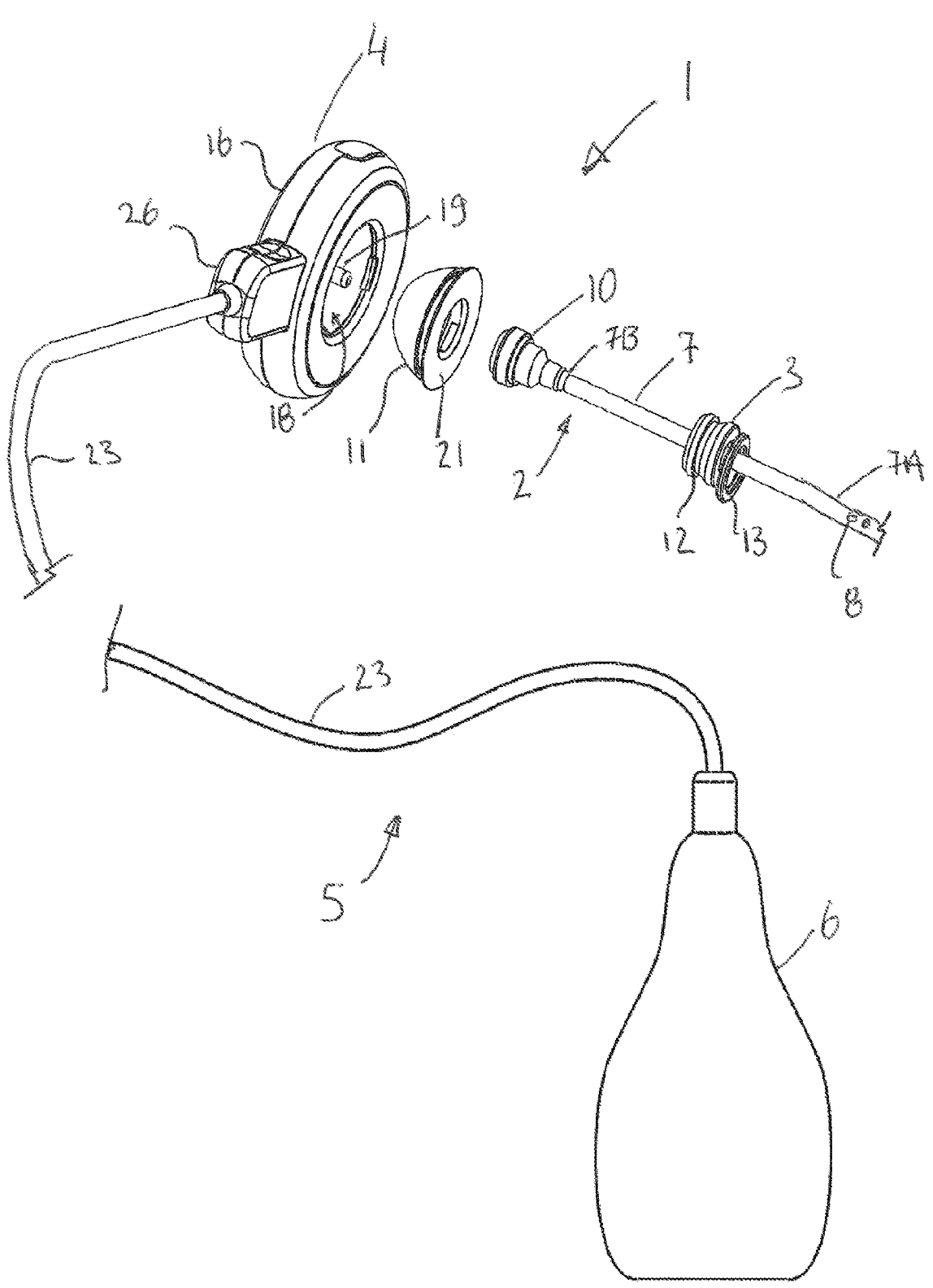
FIG. 1 is an illustration of the indwelling pleural catheter system according to the invention showing the indwelling catheter device (catheter tube and connection hub), skin anchoring member, cover for connecting hub, detachable ambulatory suction module, and pleural liquid drainage module.

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions and General Preferences

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, age, poisoning or nutritional deficiencies.

As used herein, the term "treatment" or "treating" refers to an intervention (e.g. the administration of an agent to a subject) which cures, ameliorates or lessens the symptoms of a disease or removes (or lessens the impact of) its cause(s) (for example, the reduction in accumulation of pathological levels of lysosomal enzymes). In this case, the term is used synonymously with the term "therapy".

Additionally, the terms "treatment" or "treating" refers to an intervention (e.g. the administration of an agent to a subject) which prevents or delays the onset or progression of a disease or reduces (or eradicates) its incidence within a treated population. In this case, the term treatment is used synonymously with the term "prophylaxis". A therapeutic result in this context includes eradication or lessening of symptoms, reduced pain or discomfort, prolonged survival, improved mobility and other markers of clinical improvement. A therapeutic result need not be a complete cure. Improvement may be observed in biological/molecular markers, clinical or observational improvements. In a preferred embodiment, the methods of the invention are applicable to humans, large racing animals (horses, camels, dogs), and domestic companion animals (cats and dogs).

In the context of treatment and effective amounts as defined above, the term subject (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, camels, bison, cattle, cows: primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; and rodents such as mice, rats, hamsters and guinea pigs. In preferred embodiments, the subject is a human. As used herein, the term "equine" refers to mammals of the family Equidae, which includes horses, donkeys, asses, *kiang* and zebra.

"Pleural effusion" refers to a condition characterised by a build-up of excess fluid in the pleural cavity, the cavity defined by the parietal and visceral membranes that surrounds the lungs and act to lubricate and facilitate breathing. Normally the pleural cavity contains a small amount of fluid. An excess of fluid can cause chest pain, cough, dyspnea and orthopnea. The condition can be caused by many factors, including heart failure, pulmonary embolism, cirrhosis, and open heart surgery. Other causes include pneumonia, cancer, kidney disease, and inflammatory conditions.

"Indwelling catheter device" refers to a catheter suitable for treatment of a condition characterised by a build-up of fluid in a body cavity such as a pleural or peritoneal cavity, for example pleural effusion or ascites, having a length of catheter tubing with fenestrated distal end and a connector such as a connection hub at the proximal end fluidically connected to the catheter tubing. In the case of an indwelling pleural catheter, the catheter tubing is dimensioned to pass through the chest wall and into and along the pleural cavity. The fenestrations (apertures) in the catheter tube are generally dimensioned to allow drainage of fluid from the pleural cavity through the tube under pressure.

"Connection hub" refers to a proximal part of the catheter device that is configured for fluidic coupling with the detachable ambulatory suction module (or in some embodiments to a fluid drainage device) and also anchoring the catheter device to the skin of the patient, generally by attachment to a separate anchoring member which itself is attached to the skin of the patient (although in one embodiment the anchoring member may form part of the connection hub). The connection hub comprises a closure or closures (for example one or more valves) that are configured to close when the ambulatory suction module is de-coupled from the connection hub leaving the catheter tube depressurised. The connection hub is configured for engagement with the suction module or cover in any way, for example by a snap-fit, friction fit, twist-lock engagement mechanism. In one embodiment, the connection hub comprises a base element and a through-lumen. The base may comprise formations to allow coupling the connection hub to the anchoring member.

"Skin anchoring member" refers to a device that is configured to anchor to the skin and in one embodiment couple with the connection hub. In one embodiment, it comprises a base and a spiral anchor for insertion into and under the skin by rotation of the anchoring member. Generally, the base comprises a through aperture through which the catheter tube is advanced into the pleural cavity. The base may comprise formations for coupling with the connection hub. In one embodiment, the skin anchoring member comprises an upper medical article attachment portion and a lower insertion portion for securing the anchoring member subcutaneously to a subject wherein the insertion portion comprises a spiral anchor disposed substantially in a single plane. In one embodiment, the spiral anchor defines an Archimedean spiral shape. e.g. the spiral anchor is disposed in a single plane. Preferably, the spiral anchor extends laterally outwards from the medical article attachment portion. In one embodiment, the spiral anchor comprises at least one full turn. Preferably, the spiral anchor is flexible. Preferably, the spiral anchor comprises a free insertion end for insertion in a subject. In one embodiment, the medical anchor device further comprises a skin receiving interstice between the medical article attachment portion and the spiral anchor. Preferably, the interstice comprises a slot-like interstice. Suitably, the interstice is defined by a spacer arm between the medical article attachment portion and the spiral anchor. More preferably, the spacer arm is configured to define a curved skin abutting face. In one embodiment, the curved skin abutting face comprises a concave skin abutting face. Preferably, the spacer arm comprises a non-flexible spacer arm. Suitably, the spiral anchor is attached to the medical article attachment portion at a medical article attachment portion end contiguous with the medical article attachment portion. In one embodiment, the medical article attachment portion comprises a platform. Preferably, the platform comprises a substantially cylindrical platform. More preferably, the platform comprises a lumen. The cylindrical platform may have a cross-section that is generally circular, oval, square, rectangular or any other shape. In one embodiment, the medical article attachment portion comprises adhesive for adhering the attachment portion to the subject around an incision. Most preferably, the lumen comprises a top opening and a bottom opening. Advantageously, the platform comprises a medical article mounting. Preferably, the medical article mounting comprises a top medical article mounting at the top opening. Optionally or in addition, the medical article mounting comprises a bottom medical article mounting at the bottom opening. In one embodiment, the top medical article mounting and/or the bottom medical article mounting comprises a screw thread. Other forms of mountings may be employed, such as for example re-entrant slots, friction-fit mountings, adhesive mountings, and clips or clamps.

"External housing" (or "pleural port") refers to a housing configured to couple with the connection hub and having a through lumen for receipt of the connection hub such that a top surface of the connection hub is exposed at the top of the eternal housing and is thereby accessible to the fluid inlet of the suction module. The external housing may be dimensioned to mate with the ambulatory suction module.

"Detachable ambulatory suction module" refers to device that detachably attaches to the connection hub (optionally via the external housing) having an inlet to fluidically connect with the connection hub and an outlet to connect to the pleural fluid drainage system and a fluidic conduit fluidically connecting the inlets and outlets which generally includes a negative pressure chamber configured to maintain a negative pressure in the module when the module is de-coupled from the fluid drainage system and sealed with a closure such as a valve. The negative pressure chamber generally has a volume of at least 20 cc to 30 cc. The module is configured to exert a negative pressure in the catheter device when it is decoupled from the pleural fluid drainage system. The suction module also includes means to control the negative pressure applied by the suction module when it is de-coupled from the fluid drainage system, which in one embodiment is a valve such as a bleed valve configured to dissipate negative pressure in the suction module until a target (threshold) negative pressure is obtained (e.g. air is allowed into the suction module until the threshold negative pressure is reached). In one embodiment, the means (e.g, the bleed valve) is adjustable to vary the target pressure according to the negative pressure therapy required.

"Pleural fluid drainage system" refers to a system configured for attachment to the detachable suction module and withdrawal of pleural fluid under pressure through the indwelling catheter device and suction module when they are connected. The system of the invention may include a pleural fluid drainage system. The system generally comprises a pump or other means for draining fluid (such as gravity-fed drainage or negative pressure system) from the cavity through the indwelling catheter tube, a fluid collection vessel, and associated tubing. In one embodiment, the pleural fluid drainage system is configured to perform pleural fluid drainage at a negative pressure that is greater (e.g. −120 mmHg) than the target negative pressure employed for negative pressure therapy (e.g. −90 mmHg). The pleural fluid drainage system includes a conduit fluidically connecting with the ambulatory suction module via a connector element. In one embodiment, the connector element comprises a projecting fluidic conduit configured to project into and establish fluidic connection with the fluid outlet of the ambulatory suction module. In one embodiment, the fluid outlet comprises a closure (for example a duckbill valve, cross valve, disc valve or a combination thereof) configured to be opened by the projecting fluidic conduit of the connector element.

"Ambulatory" as applied to the detachable suction module means that the device can be worn by the patient while allowing the patient to be ambulatory; in other words, the suction module is wearable and does not require the patient to be stationary, sitting down, or in bed, for use.

"Target negative pressure" means a negative pressure that is sufficient to promote pleurodesis in a pleural cavity of a patient with pleural effusion, whilst also being safe and comfortable for the patient. It will be appreciated that the target negative pressure will vary from patient to patient, depending on their clinical situation, age and health, but it is generally in the region of 20-300 mmHg, 20-200 mmHg or 20-140 mmHg. In one embodiment, the target negative pressure in the catheter tube is 20-40, 20-60, 20-80, 20-100, 20-140, 20-200, 20-300, 40-60, 40-80, 40-100, 60-80, 60-100, 60-120, 80-100, 80-120, 80-140, 100-120, 100-140, 120-140 mmHg.

Exemplification

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

Components of System

Referring to FIG. 1 an indwelling catheter system according to one embodiment of the invention is illustrated in an exploded view. The system, which is indicated generally by the reference numeral 1, comprises including an indwelling catheter device 2 with proximal connection hub 10, an anchoring member 3 (shown prior to coupling with the connection hub), a detachable ambulatory suction module 4, and an external cover 11 (pleural port) for the proximal connection hub 10, and a pleural fluid drainage system 5. The pleural fluid drainage system 5 comprises a container 6 with a pump or negatively pressurised system (not shown) and a conduit 23 with fluidic connector 26 for providing fluidic connection between the container 6 and the ambulatory suction module 4 for pressurised draining of pleural fluid from the pleural cavity through the catheter device and suction module and into the container 6.

Referring now to FIGS. 2 to 9, the components of this embodiment of the system of the invention will be described in more detail.

Figure 2:
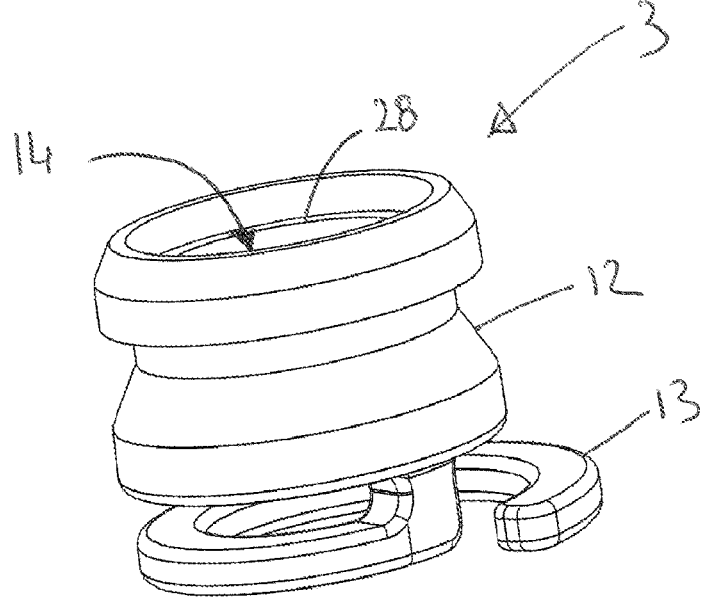
FIG. 2 is a perspective view of a skin anchoring member forming part of the system of FIG. 1.

Referring to FIG. 2, the anchoring member 3 is a spiral anchor having a base 12 and a spiral member 13 formed from a suitable elastomer such as santoprene, with a leading edge for insertion into an incision in the skin whereby rotation of the anchoring member embeds the spiral member into the skin. The base 12 comprises a through lumen 14 for receipt of the catheter device 2 and includes an annular shoulder 28 in the through lumen for coupling with connection hub 10.

Figure 3:
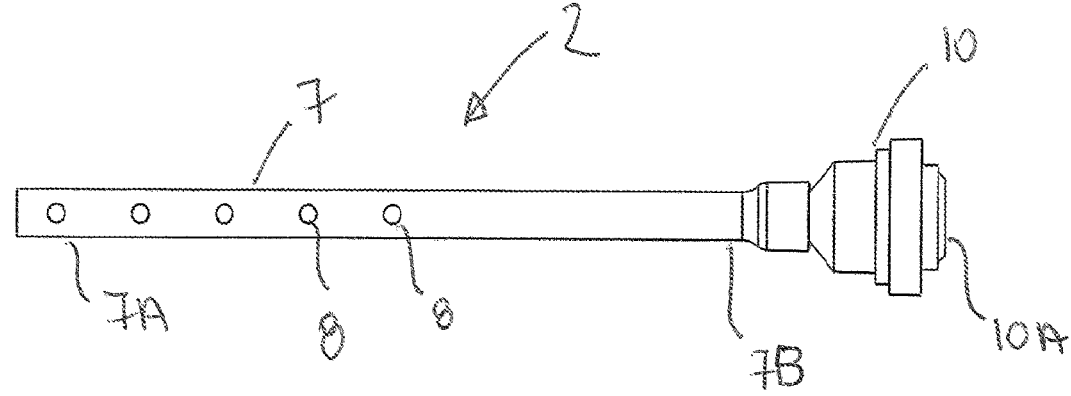
FIG. 3 is a plan view of an indwelling catheter device forming part of the system of FIG. 1 and comprising a catheter tube with a fenestrated distal end configured to reside in the pleural cavity of a subject and a connection hub.

Referring FIG. 3, the indwelling catheter device 2 comprises a silicone catheter tube 7 with a distal end 7A comprising a plurality of fenestrations 8 and a proximal end 7B terminating in the connection hub 10. The base 9 of the connecting hub 10 comprises an annular shoulder for twist-lock or push lock coupling with the through lumen 14 of the anchoring member 3. The connection hub also includes two spaced-apart valves as described in more detail below.

Figure 4:
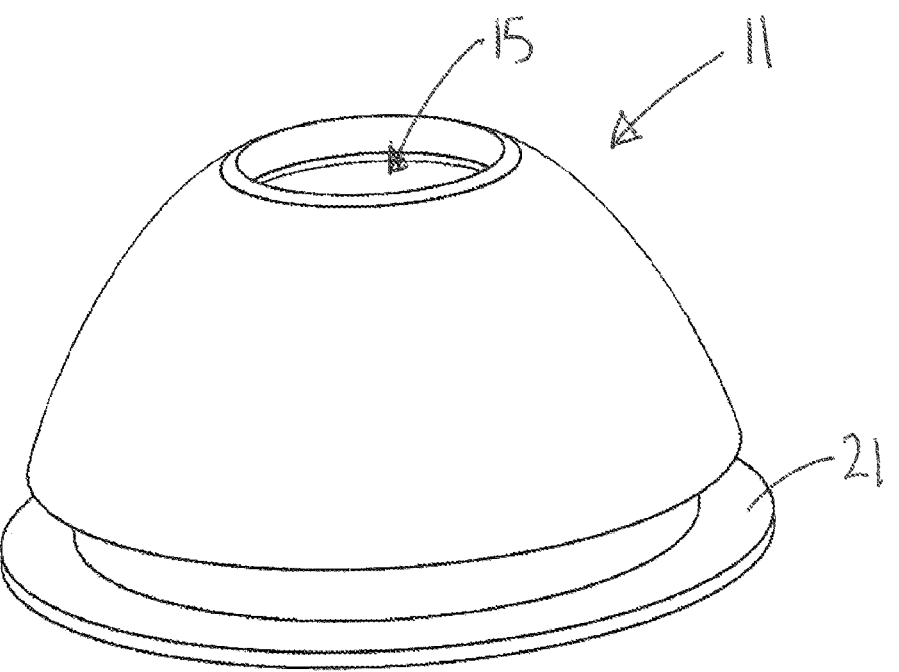
FIG. 4 is a perspective view of a detachable external housing for the connection hub forming part of the system of FIG. 1.

Referring to FIG. 4, the external housing 11 comprises a dome-shaped housing having a through lumen 15 dimensioned to receive the connection hub 10 such that the proximal end 10A of the connecting hub 10 sits generally flush with an upper surface of the external housing upon coupling of the external housing and connection hub, and an annular base element 21 configured to abut the skin around the anchoring member. The base element 21 comprises an adhesive element (not shown) for securing the base element to the skin of the subject around the anchoring member 3. The purpose of the cover is two-fold: to protect the connection hub and the incision and provide an upper surface that facilitates mating of the ambulatory suction module 4 and connection hub 10.

Figure 5:
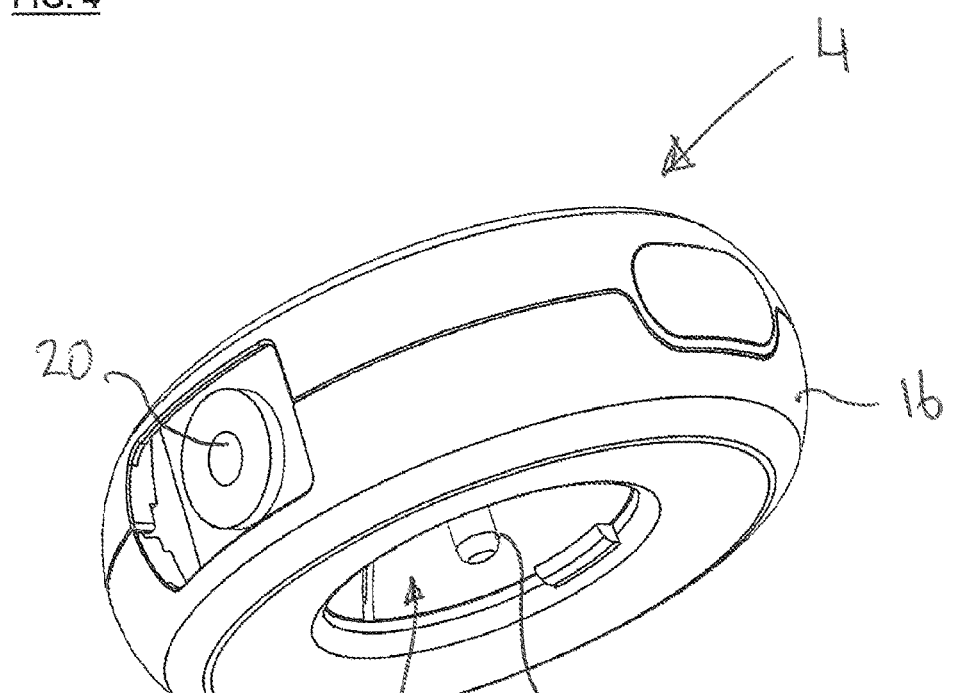
FIG. 5 is a perspective view from below of an ambulatory suction module forming part of the system of FIG. 1.
Figures 6, 7:
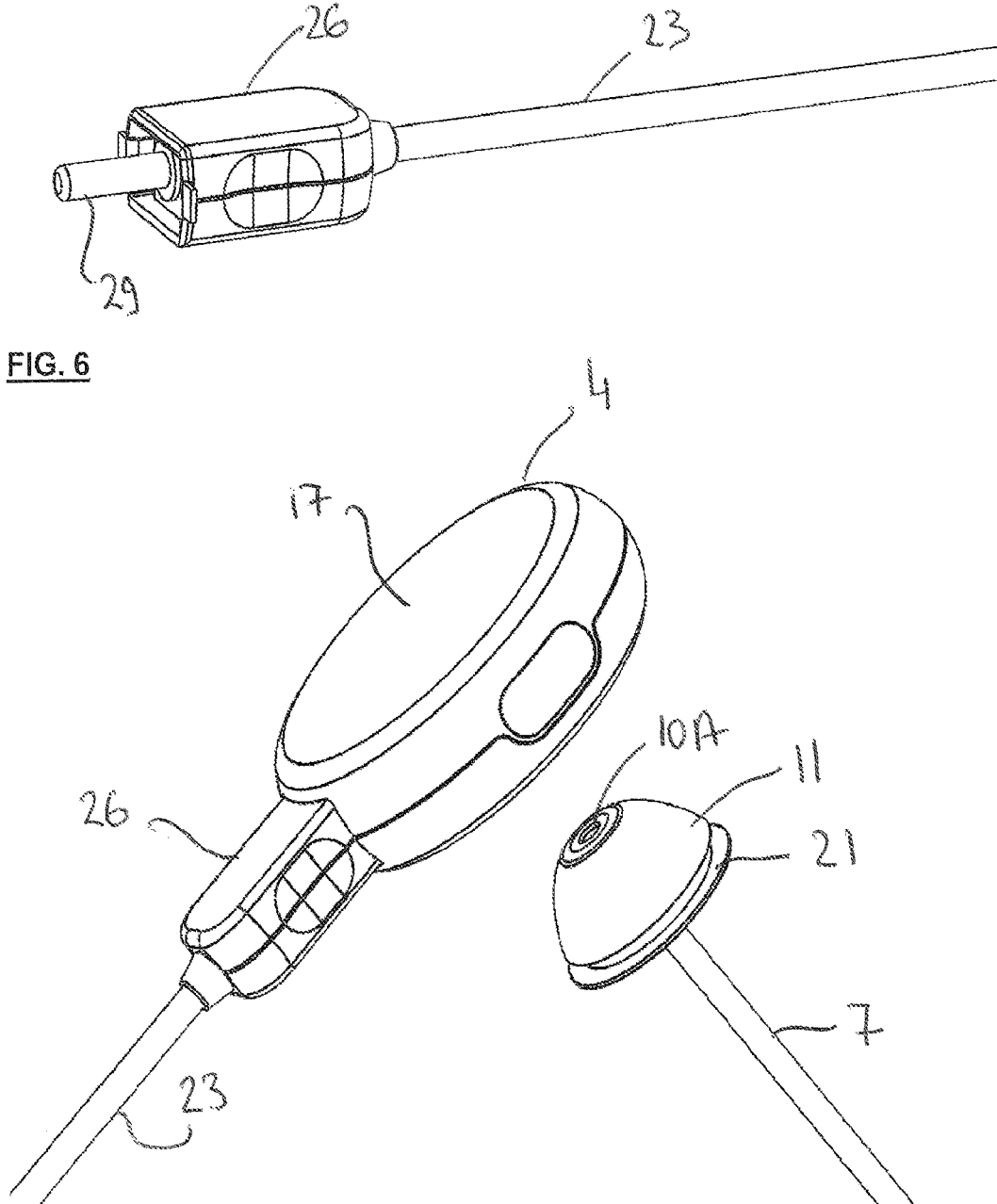
FIG. 6 illustrates a connector for connecting the pleural liquid drainage system to the ambulatory suction module.
FIG. 7 illustrates the ambulatory suction module about to be coupled and fluidically connected to the connection hub and external housing.
Figures 8, 9, 10A:
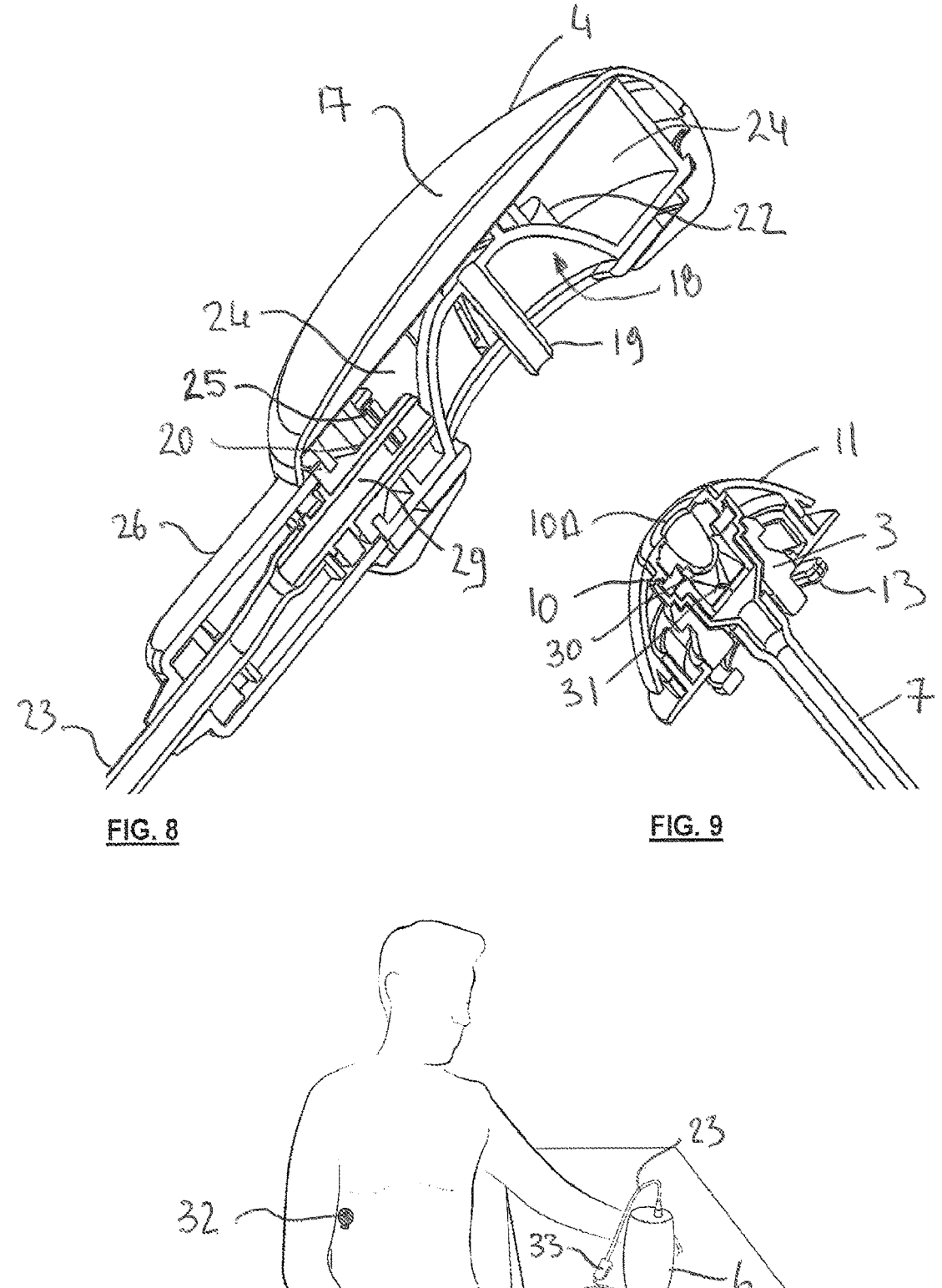

Referring to FIGS. 5, 7 and 8, the detachable ambulatory suction module 4 comprises a housing 16 having a flat top 17 and a concave underside 18 dimensioned to mate with the convex top of the external housing 11 of the connection hub 10. The housing 16 defines a fluidic channel through the module from a protruding fluid inlet 19 projecting from the concave underside 18 to a fluid outlet 20 disposed on a periphery of the module. The fluidic channel includes a negative pressure chamber 24 having a volume of approximately 30 cc. The fluid outlet 20 comprises a closure in the form of a clip 25 configured to close the fluid outlet 20 when the fluidic connector 26 of the pleural fluid drainage system 5 is de-coupled from the fluid outlet 20 to close the outlet and fluidically seal the module. A cross valve or disc valve (or a combination of a cross valve and disc valve) may also be employed as the closure. The sealing of the fluid outlet 20 combined with the pressure in the negative pressure chamber 24 results in the module being negatively pressurised and exerting a negative pressure on the pleural cavity through the catheter device 2. The module 4 also includes a bleed valve 22 configured to maintain a threshold negative pressure in the module, which in this embodiment is a negative pressure of 90 mmHg. In addition, or alternatively, the ambulatory suction module 4 or catheter tube may include a pressure sensor. The pressure sensor may be operatively coupled to the fluid drainage system 5 (e.g. to the pump of the drainage system) to modify the negative pressure exerted by the fluid drainage system based on pressure readings obtained by the pressure sensor. The sensor and drainage system may be operatively coupled to a processor, whereby the processor is configured to receive pressure readings from the pressure sensor, compare the pressure readings with a reference pressure, and modify the negative pressure exerted by the fluid drainage system based on the comparison. In one embodiment, the system is configured to prevent the negative pressure in the system and especially the ambulatory suction module dropping below negative 140 mmHg (ie negative 141 mm Hg, negative 142 mm Hg etc.). In one embodiment, the system is configured to maintain the negative pressure in the ambulatory suction module or catheter tube at a pressure of negative 20-300 mmHg, 20-200 mmHg, or 20-140 mmHg.

Referring to FIGS. 6 and 8, the fluidic connector 26 of the pleural fluid drainage system comprises a projecting conduit 29 that upon coupling of the connector 26 and ambulatory suction module 4 projects into the fluid outlet 20 forcing the clip 25 open, to open the fluid outlet of the suction module 4 and allow liquid to be drained from the pleural cavity through the catheter device and suction module 4.

FIG. 9 shows the connection hub 10, anchoring member 3 coupled to the connection hub, and external housing 11 coupled to the connection hub with a proximal end 10A of the connection hub exposed. The connection hub 10 comprises a through conduit having two spaced-apart valves, a cross valve 30 and a duck-billed valve 31. These valves are biased into a closed position to fluidically seal the connection hub and prevent fluidic passage into the catheter tube and to prevent unwanted fluidic passage out of the pleural cavity.

Referring to FIGS. 8 and 9, the connection hub 10 and ambulatory suction module 4 are illustrated prior to coupling, with the suction module 4 positioned above the connection hub 10. When the suction module 4 is moved into engagement with the connection hub, the fluid inlet 19 projects into the exposed proximal end 10A of the connection hub 10 pushing open the valves 30 and 31 to establish the fluidic communication between the ambulatory suction module and the pleural catheter. Likewise, when the suction module 4 and connection hub 10 are de-coupled, the valves close to fluidically seal the connection hub and prevent air and fluidic passage into the catheter tube.

Method of Treating Pleural Effusion

The use of the system of the invention will be illustrated with reference to FIGS. 10A to 10K.

Figure 10B:
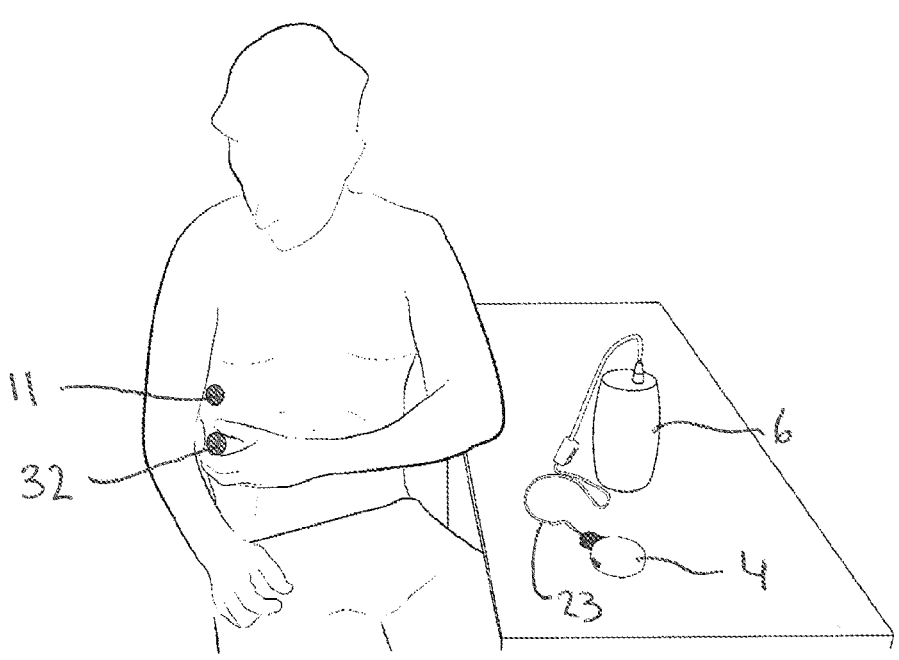
Figure 10C:
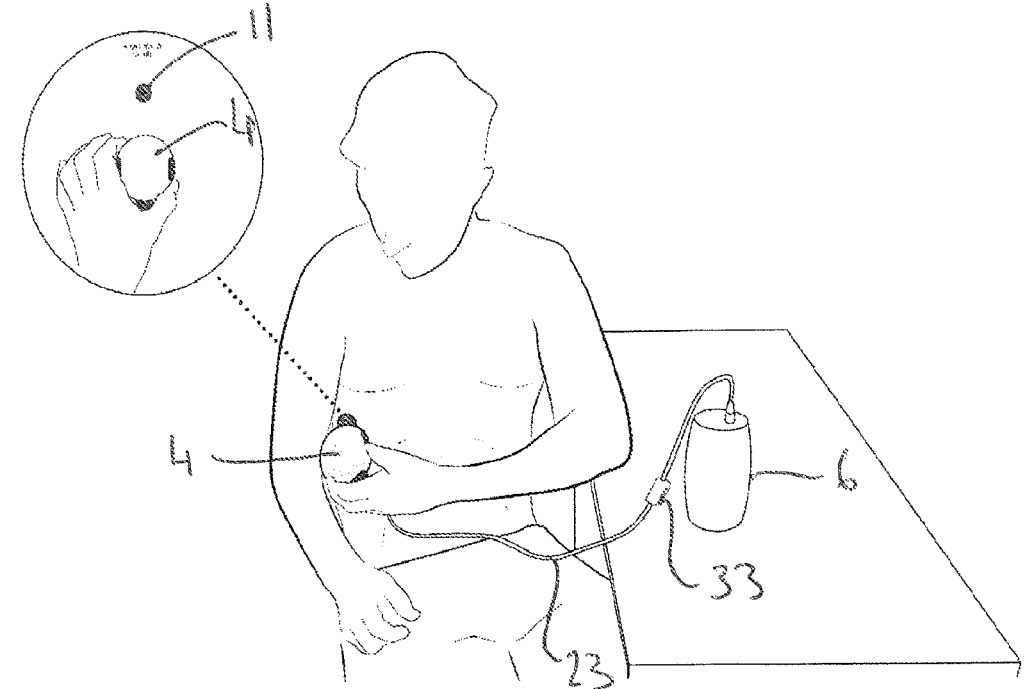

Referring initially to FIG. 10A, a patient is illustrated following placement of an indwelling catheter and anchoring member, with the connection hub and cover disposed on the surface of the patient's chest and covered by a hygiene cap 32 At this stage, the valves 30, 31 in the connection hub are closed. The suction module 4 and drainage system 5 is shown on the table behind the patient in a fluidically connected configuration. The drainage system includes a pump (not shown) and controller 33 in-line in the conduit 23. FIG. 10B shows the hygiene cap 32 being removed from the external housing by the patient.

FIG. 100 shows the suction module 4 being coupled to the connection hub by the patient. This step is facilitated by the convex shape of the external housing that matches the concave shape of the underside of the suction module. The coupling opens the valves 30, 31 in the connection hub and establishes fluidic communication between pleural catheter and suction module 4. At this stage, the pump of the drainage system has not been actuated.

Figure 10D:
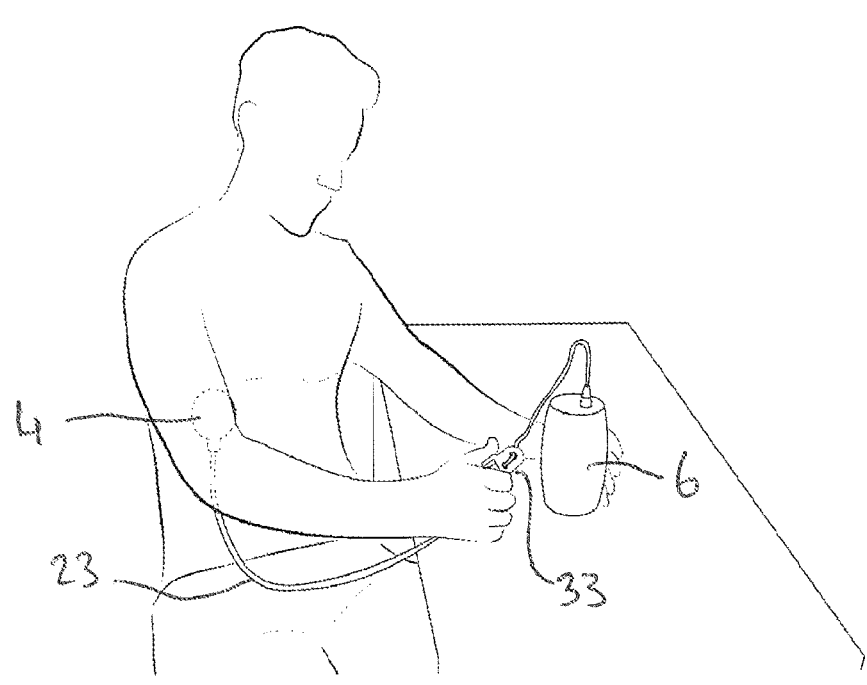

FIG. 10D shows the patient actuating the pump of the drainage system via the controller 33 to initiate the drainage step, and the drainage of fluid from the pleural cavity through the pleural catheter and suction module 4 and into the container 6.

Figure 10E:
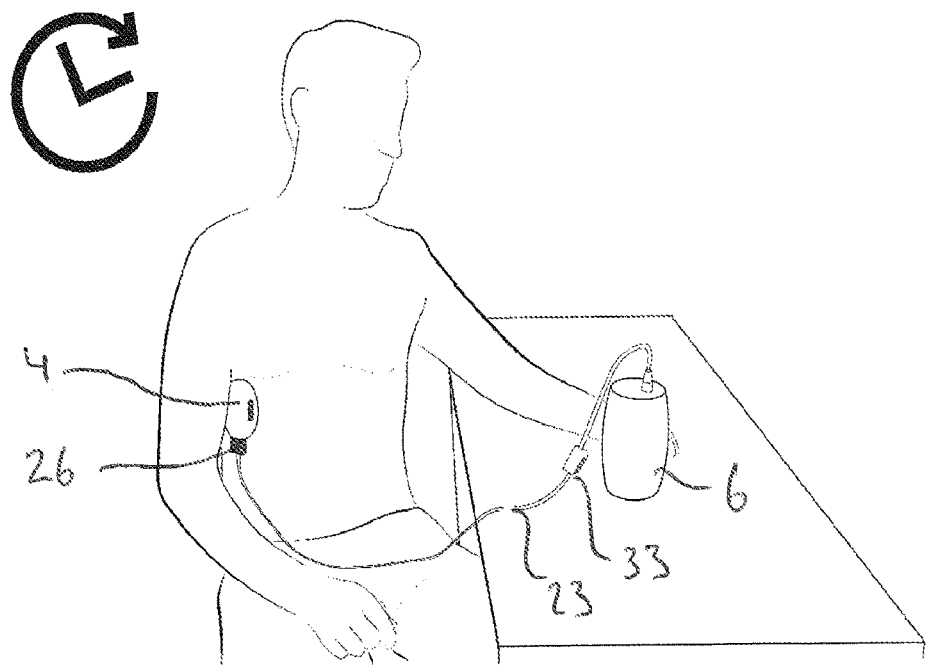

FIG. 10E illustrates the drainage step with the patient in a sitting position while the drainage step is performed.

Figure 10F:
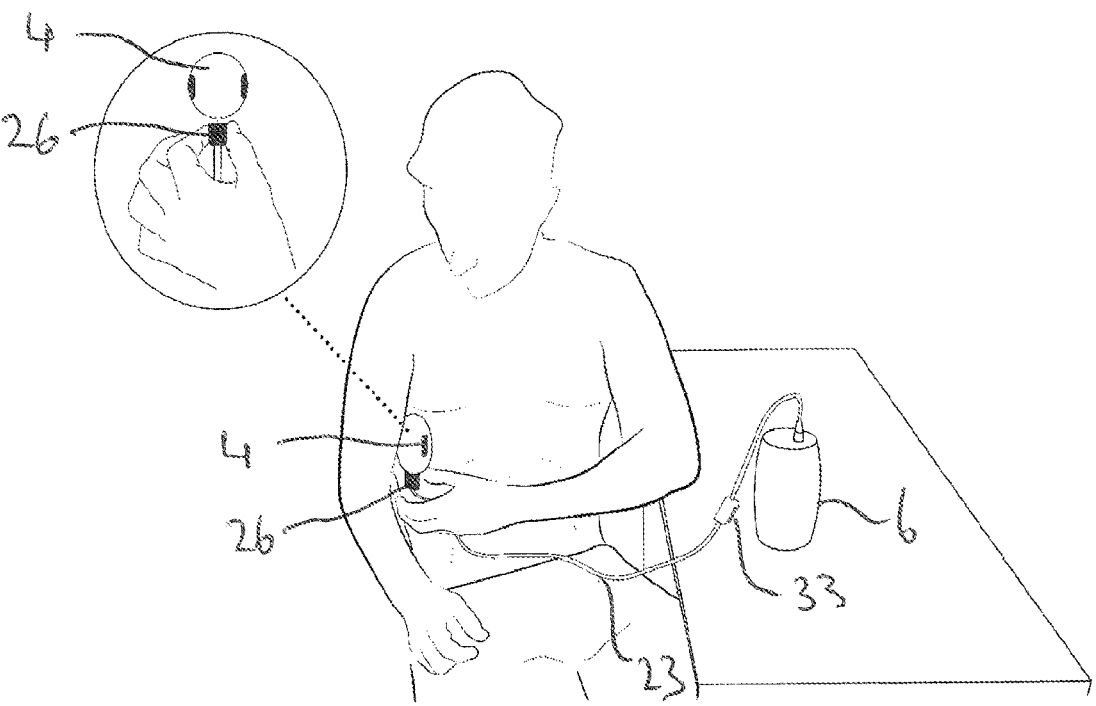

As illustrated in FIG. 10F, when the drainage step has been completed, the patient detaches the connector 26 of the pleural fluid drainage system from the ambulatory suction module 4 to terminate the drainage step and initiate the negative pressure therapy step. Upon detachment of the connector 26 from the outlet of the suction module 4, the valve in the fluid outlet of the suction module closes, maintaining a negative pressure in the suction module due to the negative pressure chamber in the suction module. The negative pressure is controlled by the bleed valve in the suction module which is designed to dissipate negative pressure if the pressure is too low by allowing air into the suction module to maintain the negative pressure at a threshold negative pressure for the duration of the negative pressure therapy step.

Figure 10G:
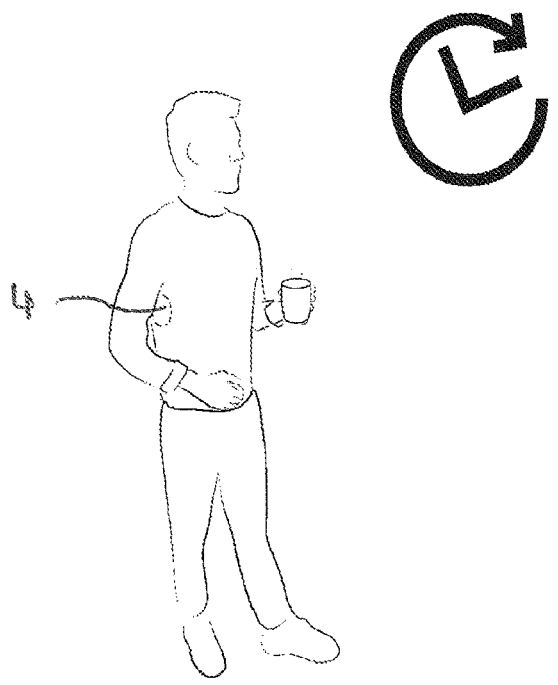
Figure 10H:
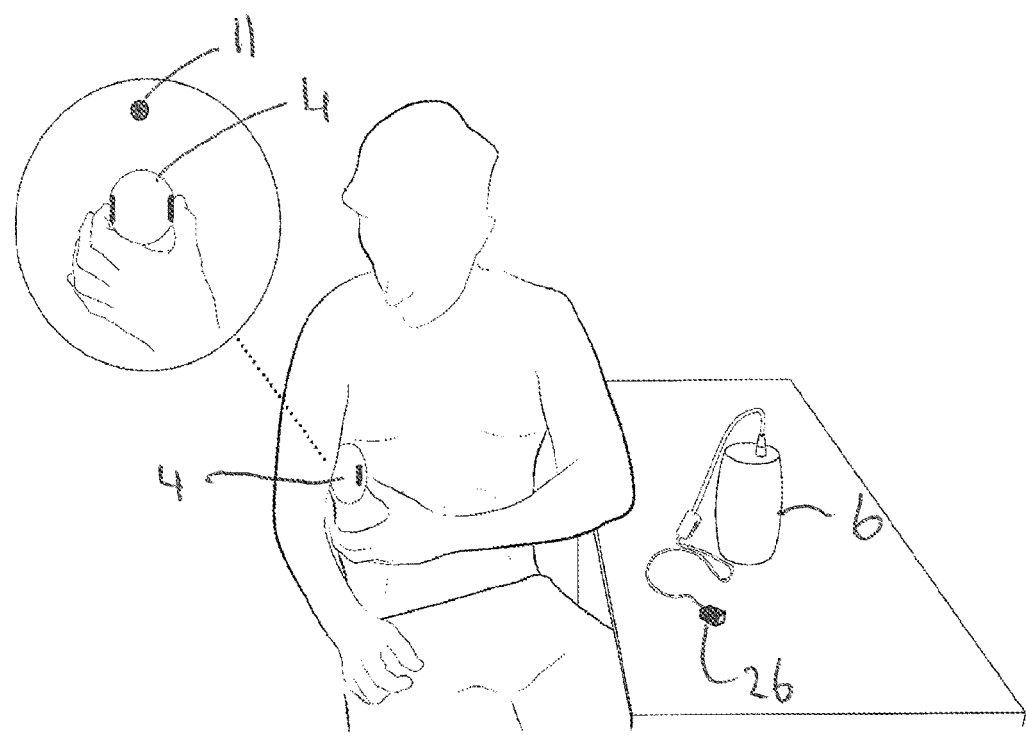

FIG. 10G illustrates the negative pressure therapy step where the ambulatory suction module remains fluidically connected to the connection hub exerting negative pressure on the pleural cavity to promote pleurodesis. During this step, the patient may be ambulatory as illustrated;

FIG. 10H illustrates the patient detaching the ambulatory suction module 4 from the connection hub 10 to terminate the negative pressure therapy step and initiate the resting step. Upon detachment the valves in the connection hub close to fluidically seal the indwelling pleural catheter.

Figure 10I:
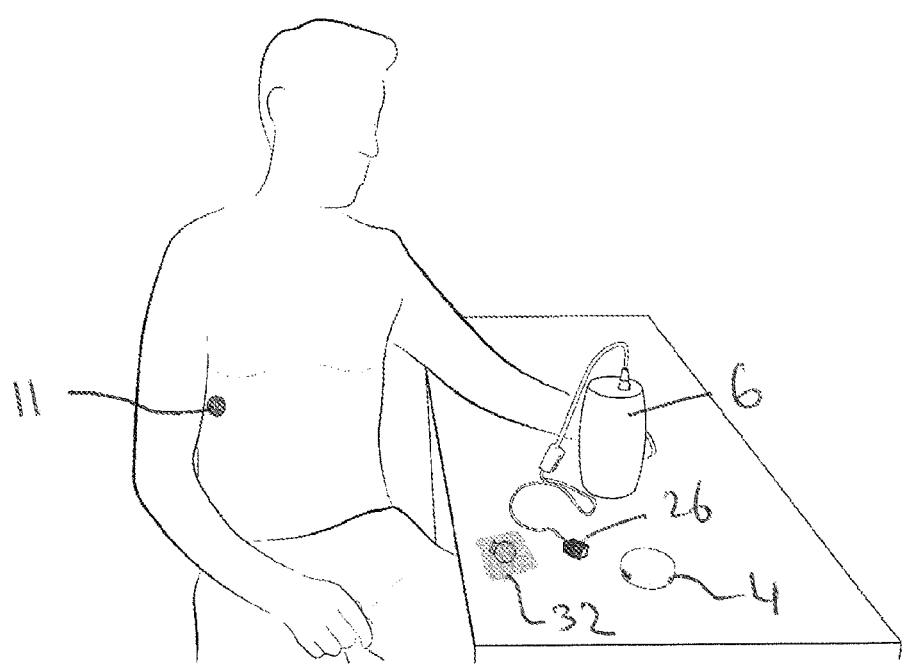
Figure 10J:
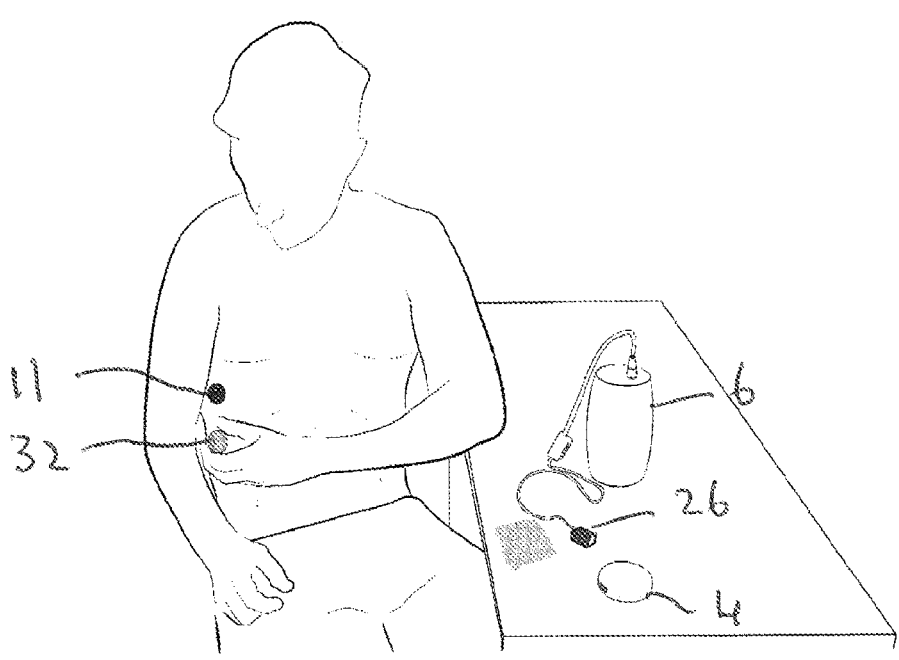
Figure 10K:
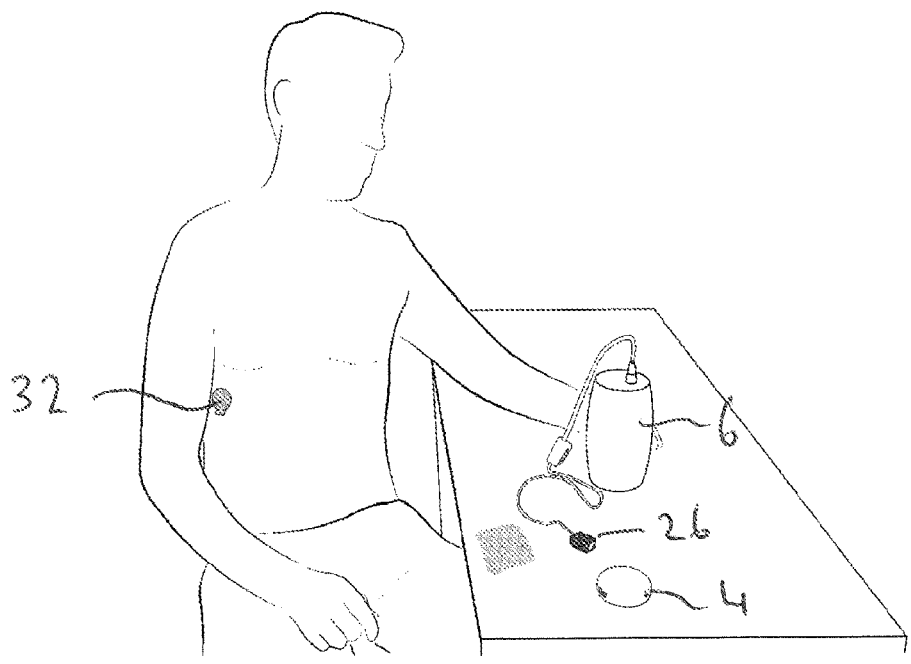

FIG. 10I shows the patient with the connection hub 10 and external housing 11 exposed and a hygiene cap 32 on the table, and FIG. 10J shows the patient about to apply the hygiene cap to the external surface of the connection hub and external housing; and FIG. 10K shows the patient during the resting step with the hygiene cap 32 covering the external surface of the connection hub and external housing. Although the patient is shown sitting, the patient may also be ambulatory during this step.

Placement of Indwelling Pleural Effusion Catheter

The placement and assembly of the system of the invention is described now in more detail. An initial incision is made in the chest of a subject, generally at a side of the chest, and the leading edge of a spiral anchor is inserted into the incision, where it is rotated to embed the anchor under the skin.

An introducer and needle/syringe are then inserted through the aperture in the spiral anchor and through the intercostal muscle and into the pleural cavity. Imaging such as ultrasound may be used to guide the advancement of the catheter safely into the pleural cavity. The needle/syringe is then removed with the introducer left in-situ. A guidewire is then advanced into the pleural cavity through the introducer and the needle/syringe is then removed.

A peel-away catheter/dilator is then advanced into the pleural cavity over the guidewire. After removal of the dilator and the guidewire the surgeon's thumb is placed over the outlet at the end of the peel-away catheter to prevent evacuation of pleural fluid.

The distal end of the catheter device is then advanced through the peel-away catheter until the connection hub abuts the peel-away catheter whereupon the peel-away catheter is removed and the connection is coupled to the spiral anchor.

The external housing (pleural port) with through-lumen is then positioned over the connection hub with the proximal end of the connecting hub exposed through the lumen and the base of the external housing secured to the subjects skin around the anchoring member.

General

The embodiment described above employs an external housing 11 that embraces the connection hub and covers the incision site, which also shrouds the connection hub with a cover configured for mating with the suction module 4. It will be appreciated that the cover is not required in some embodiments, and that the connection hub may be dimensioned to cover the incision site and provide a surface that facilitates mating with the suction module. Likewise, in the embodiments described above, the anchoring member 3 and connection hub 10 are separate elements configured for coupling together once the anchoring member has been anchored to the patient's skin. It will be appreciated that in certain embodiments, the anchoring member may form part of the connection hub and may be configured for anchoring rotation relative to the connection hub.

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. An indwelling catheter system for draining fluid from a body cavity of a subject defined by a parietal membrane and a visceral membrane, comprising:

an indwelling catheter device (2) comprising a catheter tube (7) with a fenestrated distal end (7A) configured to reside in the cavity of the subject and a connection hub (10) disposed on a proximal end (7B) of the catheter tube and configured to fluidically couple the catheter tube with a fluid drainage system;

a detachable ambulatory suction module (4) configured for detachable attachment to the connection hub (10) and comprising:

a fluid inlet (19) configured for fluidic coupling to the catheter tube (7) through the connection hub (10);

a fluid outlet (20) configured for detachable fluidic coupling to a fluid drainage system to drain pleural fluid through the detachable ambulatory suction module; and an actuable closure (25) configured to close the fluid outlet upon actuation, wherein the detachable ambulatory suction module is configured to exert a negative pressure in the catheter tube upon actuation of the closure;

an external housing (11) configured for detachable attachment to the connection hub (10) and comprising a connection hub embracing housing with a through lumen (15) for receipt of the connection hub (10) to expose a proximal end (10A) of the connection hub and a base element (21) configured to abut the skin of the subject, and wherein the detachable suction module (4) has a recessed base (18) and the external housing (11) has an upper surface dimensioned to nest within the recessed base of the detachable suction module (4).

2. The indwelling catheter system according to claim 1, wherein the base element comprises an adhesive member for attaching the external housing to the skin of the subject.

3. The indwelling catheter system according to claim 1, in which the fenestrated distal end (7A) of the catheter tube is configured to reside in the pleural cavity or peritoneal cavity of a subject.

4. The indwelling catheter system according to claim 1, wherein the actuable closure (25) is configured to close by detachment of the fluid drainage system from the detachable ambulatory suction module and open upon attachment of the fluid drainage system and the detachable ambulatory suction module.

5. The indwelling catheter system according to claim 1, in which the detachable ambulatory suction module (4) comprises a negative pressure chamber (24), wherein the fluid inlet (19) is fluidically coupled to the fluid outlet (20) by the negative pressure chamber.

6. The indwelling catheter system according to claim 5, in which the negative pressure chamber has a volume of at least 10 cc.

7. The indwelling catheter system according to claim 1, in which the detachable ambulatory suction module (4) comprises a bleed valve (22) configured to exert a threshold negative pressure in the catheter tube (7) upon detachment of the pleural fluid drainage system (5) from the detachable ambulatory suction module (4).

8. The indwelling catheter system according to claim 7, in which the bleed valve (22) is configured to maintain a threshold negative pressure in the ambulatory suction module (4) of 20-300 mmHg.

9. The indwelling catheter system according to claim 1, in which the connection hub (10) comprises a valve configured to open upon attachment of the connection hub with the detachable suction module (4) and close upon detachment of the connection hub with the detachable suction module.

10. The indwelling catheter system according to claim 1, in which the base element (21) of the external housing (11) comprises an adhesive dressing for attaching the external housing to the skin of the subject.

11. The indwelling catheter system according to claim 1, in which the fluid inlet (19) of the detachable suction module (4) projects proud of the recessed base (18) of detachable suction module (4).

12. The indwelling catheter system according to claim 1, configured for assembly into a number of different configurations including:

a resting configuration in which the detachable suction module (4) is not fluidically connected to the connection hub (10);

a drainage configuration in which the detachable suction module (4) is fluidically connected to the connection hub (10) and the fluid drainage system (5) allowing drainage of fluid under pressure through the catheter device (2) and detachable ambulatory suction module (4); and a negative pressure therapy configuration in which the detachable suction module (4) is fluidically coupled to the connection hub (10), not fluidically coupled to the fluid drainage system (5), and negatively pressurized.

13. The indwelling catheter system according to claim 1, including a fluid drainage system (5) configured for fluidic coupling to the outlet (20) of the detachable suction module (4), the fluid drainage system comprising a fluid collection vessel (6) and a pump or negatively pressurised drainage mechanism.

14. The indwelling catheter system according to claim 13, in which the fluid drainage system comprises a connector with a projecting conduit configured to project into the fluid outlet of the ambulatory suction module and open the actuable closure.

15. The indwelling catheter system according to claim 1, in which the actuable closure comprises a duck bill valve.

16. The indwelling catheter system according to claim 1, in which the connection hub (10) and/or external housing (11) comprise a UV light configured to direct light on the catheter tube and/or the subject skin at the incision or an antibacterial coating.

17. An indwelling pleural catheter system comprising:

an indwelling catheter device comprising a catheter tube with a fenestrated distal end configured to reside in the pleural or peritoneal cavity of a subject and a connection hub fluidically coupled to a proximal end of the catheter tube;

a detachable ambulatory suction module configured for detachable attachment to the connection hub and comprising:

a fluid inlet configured for fluidic coupling to the catheter tube through the connection hub;

a fluid outlet configured for detachable fluidic coupling to a pleural fluid drainage system to drain pleural fluid through the detachable ambulatory suction module; and an actuable closure configured to close the fluid outlet upon actuation, wherein the detachable ambulatory suction module is configured to exert a negative pressure in the catheter tube upon actuation of the closure;

an external housing (11) configured for detachable attachment to the connection hub (10) and comprising a connection hub embracing housing with a through lumen (15) for receipt of the connection hub (10) to expose a proximal end (10A) of the connection hub and a base element (21) configured to abut the skin of the subject, and wherein the detachable suction module (4) has a recessed base (18) and the external housing (11) has an upper surface dimensioned to nest within the recessed base of the detachable suction module (4).

18. The indwelling pleural catheter system according to claim 17, in which the detachable ambulatory suction module comprises a negative pressure chamber, wherein the fluid inlet is fluidically coupled to the fluid outlet by the negative pressure chamber.

19. The indwelling pleural catheter system according to claim 17, wherein the actuable closure (25) is configured to close by detachment of the fluid drainage system from the detachable ambulatory suction module and open upon attachment of the fluid drainage system and the detachable ambulatory suction module.

20. The indwelling pleural catheter system according to claim 18, in which the negative pressure chamber has a volume of at least 10 cc.

21. An indwelling pleural catheter system according to claim 17, in which the detachable ambulatory suction module (4) comprises a bleed valve (22) configured to exert a threshold negative pressure in the catheter tube (7) upon detachment of the pleural fluid drainage system (5) from the detachable ambulatory suction module (4).

22. The indwelling pleural catheter system according to claim 21, in which the bleed valve (22) is configured to maintain a threshold negative pressure in the ambulatory suction module (4) of 20-300 mmHg.

23. The indwelling pleural catheter system according to claim 20, in which the connection hub (10) comprises a valve configured to open upon attachment of the connection hub with the detachable suction module (4) and close upon detachment of the connection hub with the detachable suction module.

24. The indwelling pleural catheter system according to claim 17, in which a skin anchoring member (3) to anchor the connection hub to the skin of a subject is separate from and configured for coupling with the connection hub (10).

25. The indwelling pleural catheter system according to claim 24, in which the skin anchoring member (3) comprises a through-lumen (14) for receipt of the fenestrated catheter tube.

* * * * *